United States Patent
Hasan et al.

(10) Patent No.: US 9,041,532 B1
(45) Date of Patent: May 26, 2015

(54) METHODS AND SYSTEMS FOR MANAGING WIRELESS DEVICES

(71) Applicant: General Electric Company, Schenectady, NY (US)

(72) Inventors: SM Shajedul Hasan, Rexford, NY (US); David Michael Davenport, Niskayuna, NY (US); Steven William Wik, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 24 days.

(21) Appl. No.: 14/071,764

(22) Filed: Nov. 5, 2013

(51) Int. Cl.
| G08B 1/08 | (2006.01) |
| A61B 5/00 | (2006.01) |
| G01B 21/16 | (2006.01) |
| G08B 21/24 | (2006.01) |

(52) U.S. Cl.
CPC ............. *A61B 5/6844* (2013.01); *G01B 21/16* (2013.01); *A61B 5/002* (2013.01); *G08B 21/24* (2013.01)

(58) Field of Classification Search
CPC ................................ G08B 21/16; G08B 21/24
USPC ............. 340/539.12, 539.11, 501, 506, 10.1, 340/540, 541, 572.4, 572.7
See application file for complete search history.

(56) References Cited

U.S. PATENT DOCUMENTS

| 7,148,801 | B2 | 12/2006 | Crabtree et al. |
| 7,714,710 | B2 | 5/2010 | Schwartz |
| 8,102,316 | B1 | 1/2012 | Brucker et al. |
| 8,126,680 | B2 | 2/2012 | Troxler et al. |
| 2008/0092638 | A1* | 4/2008 | Brenneman et al. ......... 73/61.41 |
| 2008/0300572 | A1* | 12/2008 | Rankers et al. ............... 604/504 |
| 2009/0186577 | A1 | 7/2009 | Ross et al. |
| 2010/0265131 | A1 | 10/2010 | Fabius |
| 2011/0228727 | A1 | 9/2011 | Julo et al. |
| 2012/0154138 | A1* | 6/2012 | Cohn et al. .................... 340/501 |
| 2012/0235860 | A1 | 9/2012 | Ghazarian |

FOREIGN PATENT DOCUMENTS

| GB | 2474282 A | 4/2011 |
| WO | 2009109779 A1 | 9/2009 |
| WO | 2012095829 A2 | 7/2012 |

* cited by examiner

*Primary Examiner* — Tai T Nguyen
(74) *Attorney, Agent, or Firm* — Scott J. Asmus

(57) ABSTRACT

Systems and methods for managing patient monitoring devices are disclosed. Patient information is transmitted from a patient sensor operatively coupled to a patient to a patient monitor. The patient sensor and the patient monitor are communicatively coupled over a communications network available in a designated monitoring area. Further, loss of the patient sensor from the designated monitoring area is detected by one or more of the patient sensor, the patient monitor and a user. One or more loss prevention indicators are initiated at the patient sensor upon detecting the loss of the patient sensor. Additionally, the loss prevention indicators are communicated to indicate location of the lost patient sensor.

22 Claims, 4 Drawing Sheets

METHODS AND SYSTEMS FOR MANAGING WIRELESS DEVICES

BACKGROUND

Embodiments of the present disclosure relate generally to wireless networks for patient monitoring and, more particularly, to systems and methods for preventing loss of wireless sensor devices.

Real-time access to comprehensive patient information at the point of care facilitates early detection of deterioration of health of a patient, thus allowing for timely intervention and/or making informed clinical decisions. Accordingly, a patient care facility may employ a plurality of sensing devices that periodically determine physiological indicators such as respiration, heartbeat, blood pressure, oxygen saturation (SpO2), limb motion, and features of an electrocardiogram (ECG) for ascertaining the health of the patient.

Conventionally, the sensing devices are connected to the patient through wires, catheters, and/or tubing. However, use of the conventional wired sensing devices may hinder movement of the patient in and around a hospital room, while also restricting a caregiver's access to the patient. Furthermore, wired sensing devices may complicate provision of varying levels of patient care, for example, progressing from low-acuity monitoring at admission to high-acuity monitoring within a specialized care unit, to a lower-acuity monitoring until discharge. Such an evolving regime of patient care may entail recurrent addition and/or removal of sensing devices connected to the patient, thereby resulting in cable clutter and procedural delays caused by unnecessary time spent in cable and device management.

Use of wireless sensors operatively coupled to the patient to transmit patient information over a wireless network circumvents at least some of the issues associated with cable clutter and device management. Typical wireless sensors are small, lightweight, and are often body-worn to allow for enhanced ambulation of patients, while providing accurate measurements of physiological indicators to a designated patient monitoring system. Particularly, the wireless sensors may be configured to communicate with the designated patient monitoring system over a spectrum of bandwidths defined by an appropriate regulatory authority.

However, in absence of cables, a caregiver lacks visual cues associated with the cables to assure that the wireless sensors are appropriately connected and are communicating patient information only to the designated monitoring device. Furthermore, the small and lightweight wireless sensors may get lost within or outside the hospital room. For example, the wireless sensors may detach from the patient and may get lost during cleaning in a laundry chute, in the bathroom, under the bed, due to theft, or unintentional inventory movement. The absence of cables and the small size may delay detection of the loss of the wireless sensors, thus resulting in loss of patient information. Moreover, movement of lost wireless sensors, which are communicating over a shared radio frequency spectrum, may lead to undesirable interference with other wireless sensors or other radio systems in use within the hospital environment.

Accordingly, certain wireless patient monitoring systems employ tracking systems for locating wireless sensors. For example, some wireless systems may employ real-time locating system (RTLS), global positioning system (GPS), infrared (IR) units, and/or radio frequency identifier (RFID) technology for tracking and/or locating wireless devices. However, such conventional wireless tracking systems employ additional infrastructure and/or devices such as RFID tags and IR sensors to locate the wireless sensors. Alternatively, certain systems employ a telecommunications base station for locating the wireless sensors using a beacon signal and triangulation. In such systems, locations of the wireless sensors may be determined only at the RTLS system, the GPS device, and/or the base station. Furthermore, the conventional tracking systems may not allow a user to locate lost wireless sensors that have lost communication with corresponding GPS, RTLS, or central communications system.

BRIEF DESCRIPTION

In accordance with aspects of the present disclosure, a patient sensor is disclosed. The patient sensor includes a sensor transceiver configured to transmit patient information to a patient monitor over a communications network available in a designated monitoring area. Further, the patient sensor includes a sensor processing unit configured to initiate one or more loss prevention indicators upon receiving a reveal signal from the patient monitor and/or upon failing to receive communication from the patient monitor for more than a determined period of time. The patient sensor also includes one or more sensor output devices configured to communicate the loss prevention indicators to indicate location of the lost patient sensor.

In accordance with another aspect of the present disclosure, a method for managing patient monitoring devices is presented. Patient information is transmitted from a patient sensor operatively coupled to a patient to a patient monitor. The patient sensor and the patient monitor are communicatively coupled over a communications network available in a designated monitoring area. Further, loss of the patient sensor from the designated monitoring area is detected by one or more of the patient sensor, the patient monitor and a user. One or more loss prevention indicators are initiated at the patient sensor upon detecting the loss of the patient sensor. Additionally, the loss prevention indicators are communicated to indicate location of the lost patient sensor.

In accordance with certain further aspects of the present disclosure, a patient monitor, a patient interrogator, a sensor network, and a non-transitory computer readable medium that stores instructions executable by one or more processors to perform a method for managing patient monitoring devices are also disclosed.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

The following description presents systems and methods for management of patient monitoring devices. Particularly, certain embodiments illustrated herein describe systems and methods for preventing loss of wireless sensors from a designated monitoring area. Although certain conventional systems for tracking of wireless devices are known, these conventional systems employ additional communication infrastructure and/or tracking devices such as RFID tags and GPS receivers. Use of conventional tracking systems, thus, is expensive and entails additional programming and network setup. In contrast, embodiments of the present disclosure describe cost-effective and uncomplicated procedures that detect loss of the wireless sensors and aid in automatically locating and/or retrieving the wireless sensors using existing wireless communications infrastructure.

Although the following description includes embodiments relating to wireless patient monitoring in a hospital environment, these embodiments may also be implemented in other patient monitoring scenarios. For example, the embodiments of the present disclosure may be implemented for monitoring the patient in a clinic, at home, and/or in a mobile unit setting. An exemplary environment that is suitable for practicing various implementations of the present disclosure is described in the following sections with reference to FIG. 1.

Figure 1:
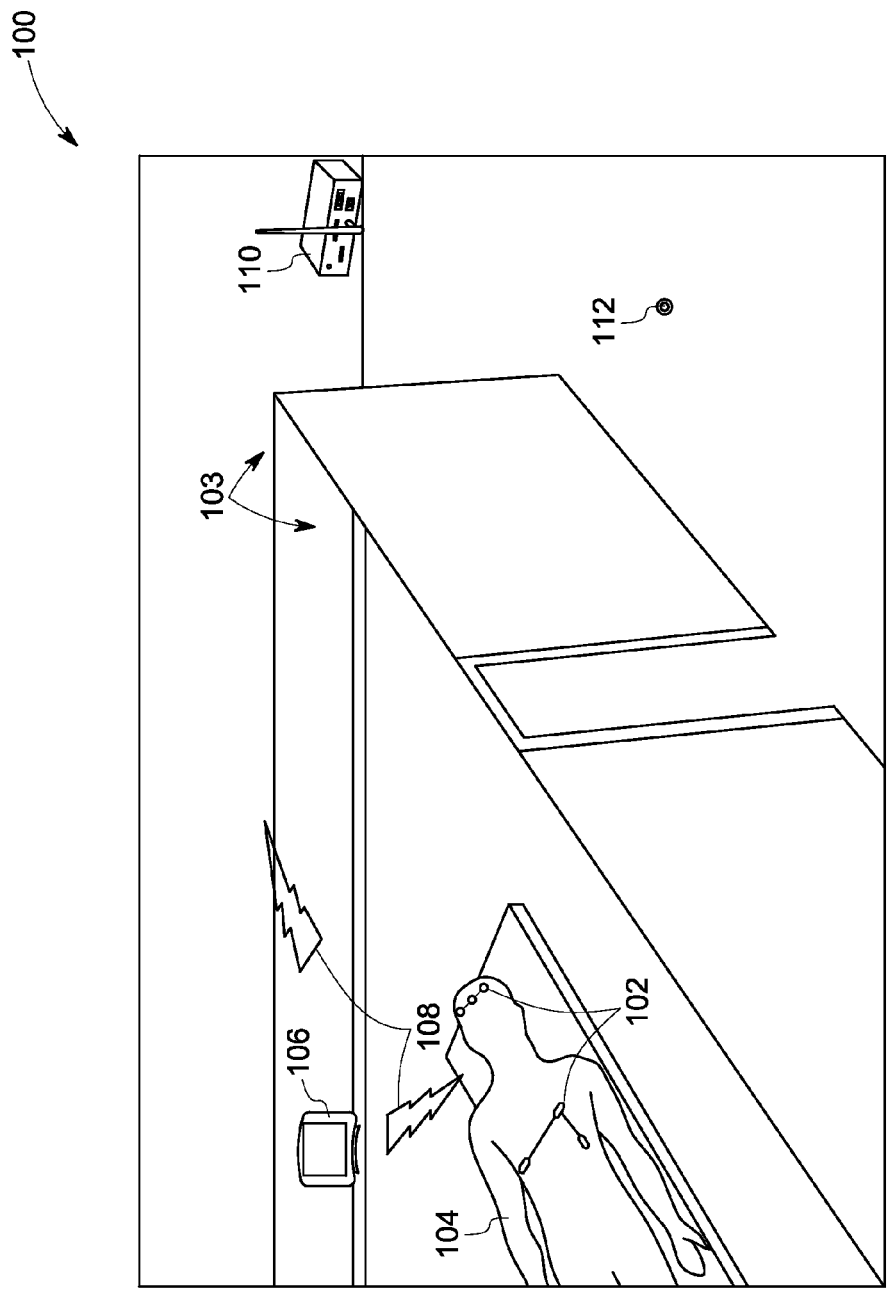
FIG. 1 is a schematic diagram of an exemplary system for managing patient monitoring devices, in accordance with aspects of the present disclosure.

FIG. 1 illustrates an exemplary system 100 configured for managing patient monitoring devices such as one or more wireless patient monitoring sensors 102 within a designated monitoring area 103. The designated monitoring area 103, for example, includes a hospital room that houses a patient 104 being monitored and/or one or more other regions within the hospital to which one or more of the sensors 102 may be mistakenly moved such as hospital corridors, elevator lobbies, patient lounges, cafeterias, laundry room, and/or kitchen. Alternatively, the designated monitoring area 103 may correspond to one or more regions within and/or outside a room in the patient's home, an assisted living facility, and/or a mobile medical unit where the sensors 102 may be used.

In one embodiment, the sensors 102 include wearable devices that may be physically connected to a desired region of the patient 104 for monitoring medically relevant information. Alternatively, the sensors 102 may correspond to sensing devices, such as optical sensors, that are configured to monitor the patient information non-invasively. Moreover, the sensors 102 may be configured to measure one or more physiological indicators of the patient 104 continuously, at random points of time, or after designated intervals of time. Additionally, in certain embodiments, one or more of the sensors 102 may be configured to monitor ambient environmental conditions such as temperature, sound, and light that may affect rest and recovery of the patient 104.

Accordingly, the sensors 102 may include electrical surface potential sensors, bio-impedance sensors, accelerometer-based motion detectors, capacitive sensors, optical sensors, RF sensors, passive IR (PIR) sensors, and/or other suitable sensors. These sensors 102 may be configured to monitor physiological indicators such as heartbeat, respiration, blood pressure, SpO2, limb motion and/or features of an ECG, and/or an electroencephalogram (EEG). Additionally, some of the sensors 104 may measure other medically relevant information, for example, a level of a desired biological material such as hormones and/or non-biological material such as a contrast agent in the patient's body.

In one embodiment, the sensors 102 communicate the medically relevant information to a designated patient monitor 106 communicatively coupled to the sensors 102 over a wired and/or wireless communications network 108 available in the designated monitoring area 103. The monitor 106 communicates the received information to allow a caregiver such as medical practitioner, a doctor, a nurse, and/or an attendant to ascertain a current state of patient health and well-being. To that end, the monitor 106, for example, may continually display the received information on an associated display. The caregiver may use the displayed information to ascertain the patient state. Moreover, the caregiver may modify dosage of a medicine, adjust ambient conditions, update a patient chart, and/or further communicate the information, for example, to a medical specialist and/or a remote hospital information system (HIS) based on the ascertained patient state.

Continual access to patient information measured by the sensors 102, thus, greatly facilitates clinical diagnosis, in turn, allowing for faster recovery. Accordingly, a frequency and/or time interval for receiving patient information at the monitor 106 from each of the sensors 102 may be pre-programmed into the system 100 and/or may be selectively configured by the caregiver based on monitoring requirements. For example, in one embodiment, the monitor 106 may receive the patient information from one or more of the sensors 102 continuously. In another embodiment, however, the monitor 106 may receive the patient information periodically at desired intervals of time such as every few minutes. In yet another embodiment, the monitor 106 may receive the patient information non-periodically. In certain further embodiments, the monitor 106 may receive the patient information when one or more of the sensors 102 detect a predetermined signal or condition reflecting patient status. For example, one of the sensors 102 may transmit the patient information to the monitor 106 upon detecting that a respiration rate of the patient is approaching or is below a determined respiration threshold.

One or more of the sensors 102, however, may detach from the patient 104 and lose communications with the monitor 106 due to unintentional movement of the sensors 102, for example, during delivery of food, housekeeping, and/or ambulation of the patient 104 within or outside the hospital room. One or more of the sensors 102 may also lose communications with the monitor 106 if the sensor 102 is detached from the first patient 104 and is operatively coupled to a second patient without completing a predefined termination sequence with the monitor 106. In accordance with aspects of the present disclosure, absence of communication between one or more of the sensors 102 and the monitor 106 for more than a determined period of time may be indicative of a loss of the corresponding sensors 102.

In one embodiment, the loss of communication may be determined by either the monitor 106 and/or a lost sensor 112. Accordingly, either or both of the monitor 106 and the lost sensor 112 may initiate specified loss prevention procedures. For example, the monitor 106 may initiate the loss prevention procedures upon detecting absence of communications between the lost sensor 112 and the monitor 106 for more than the determined period of time. The monitor 106 may also initiate the loss prevention procedures based on an input received from a caregiver. Further, the lost sensor 112 may initiate the loss prevention procedures upon detecting absence of communications between the lost sensor 112 and the monitor 106 for more than the determined period of time. The lost sensor 112 may also initiate the loss prevention procedures when a link establishment procedure between one of the lost sensor 112 and another monitor is initiated without completing the predefined termination sequence with the monitor 106. Thus, in certain embodiments, the system 100 combines link management with the loss prevention procedures to allow for efficient device management.

Specifically, in one embodiment, the monitor 106 transmits a reveal signal to the lost sensor 112 to instruct the lost sensor 112 to initiate loss prevention indicators. The loss prevention indicators, for example, may include generating an audible alarm, blinking lights, and/or vibrating. Additionally, the monitor 106 may communicate the loss of the sensor 112 to the caregiver, for example, through an audible alarm or visually by displaying an alert on the associated display. In certain embodiments, the monitor 106 may be configured to transmit an alert message indicating the loss of the sensor 112 via an email, a short messaging service (sms), and/or a popup to a remotely connected system such as the HIS or to a predefined mobile phone number.

However, if the sensor 112 moves outside a communications range of the monitor 106, the lost sensor 112 may be unable to receive the reveal signal transmitted by the monitor 106. Accordingly, in one embodiment, when the monitor 106 fails to receive any response to the reveal signal within a determined time interval or after a determined number of communication attempts, the monitor 106 assumes the sensor 112 to be lost outside an immediate patient monitoring region such as the hospital room.

Subsequently, the monitor 106 communicates the loss of the sensor 112 to at least one interrogator 110 communicatively coupled to the monitor 106 over the same communications network 108. Additionally, in certain embodiments, the monitor 106 provides the interrogator with association information such as frequency range and/or authentication parameters that would allow the interrogator 110 to establish communications with the lost sensor 112. Alternatively, the interrogator 110 may use default association parameters that may be available to all devices connected over the communications network 108 to allow limited communications between the interrogator 110 and the lost sensor 112. Accordingly, the interrogator 110 uses the received or the default association information to transmit a reveal signal to the lost sensor 112 to instruct the lost sensor 112 to initiate loss prevention indicators.

Additionally, the present disclosure also allows for detection and retrieval of the lost sensor 112 even when the sensor 112 is unable to communicate with the interrogator 110 due to loss of connectivity to the wireless network 108. Particularly, one embodiment allows the lost sensor 112 to independently determine a loss of communication with the monitor 106 for more than a determined period of time. Upon determining the loss of communications, the sensor 112 may immediately initiate the loss prevention indicators to allow a caregiver to identify a location of the lost sensor 112.

Embodiments of the present disclosure, thus, provide a simple and cost-effective system 100 for preventing loss of the patient monitoring sensors 102 without use of additional network infrastructure or any additional location-specific sensors. Particularly, the embodiments described herein expand the use of an existing wired and/or wireless communications network 108 to aid in detection and retrieval of the lost sensor 112 by allowing for intelligent initiation of the loss prevention indicators. Certain exemplary components of a wireless patient monitoring system configured to prevent loss of wireless devices, in accordance with aspects of the present disclosure, are described in greater detail with reference to FIG. 2.

Figure 2:
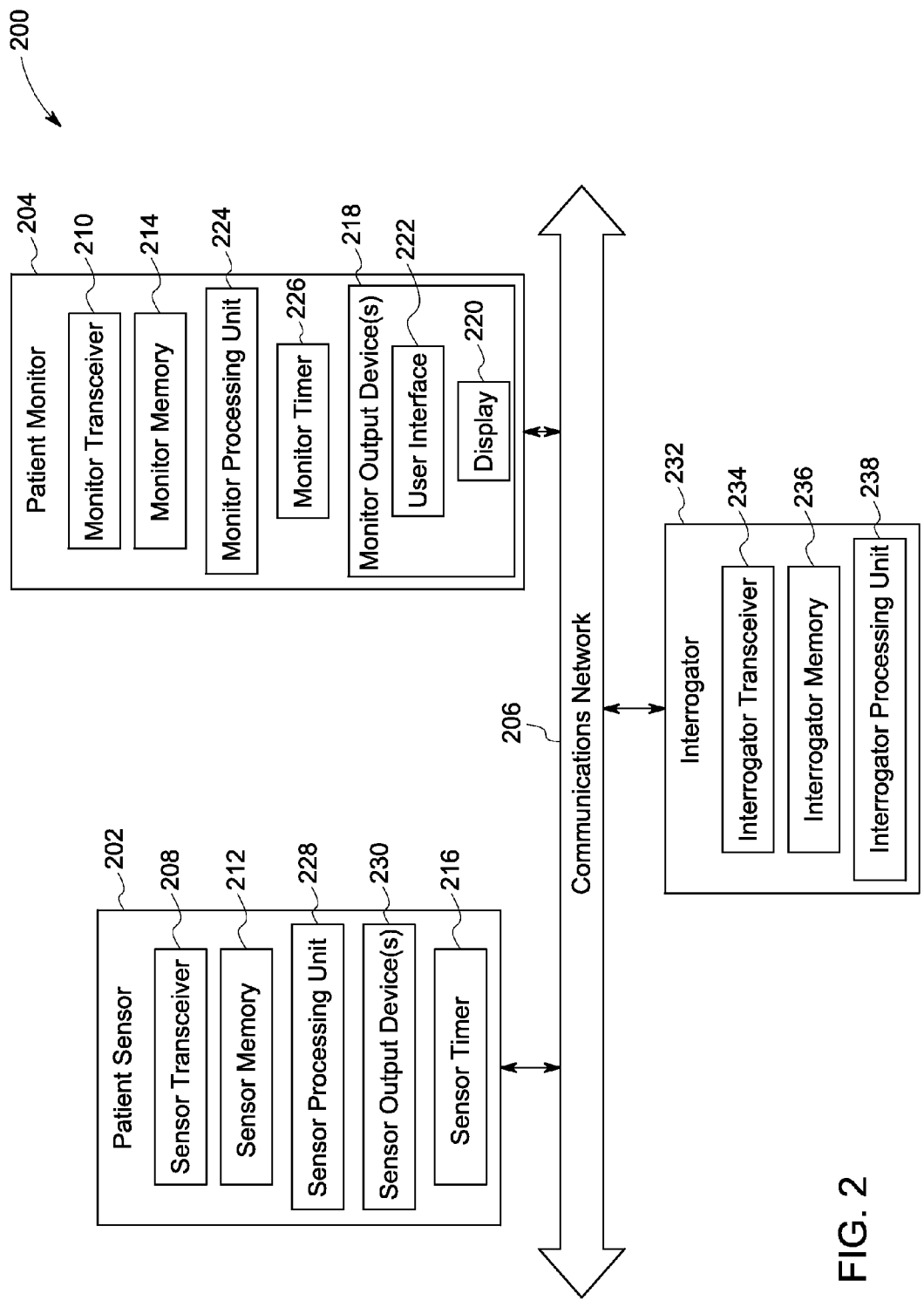
FIG. 2 is a block diagram of exemplary components of a patient monitoring system, in accordance with aspects of the present disclosure.

FIG. 2 illustrates a block schematic diagram of certain exemplary components of a wireless patient monitoring system 200 similar to the system 100 of FIG. 1. The system 200 includes a patient sensor 202, similar to the sensors 102 of FIG. 1, communicatively coupled to a patient monitor 204, similar to the monitor 106 of FIG. 1, over a communications network 206. In one embodiment, the communications network 206 corresponds to a network infrastructure already existing in a designated monitoring area such as hospital premises, home, clinic, or in an ambulance. Accordingly, the communications network 206, for example, includes a wired network, a wireless body area network (BAN), a wireless personal area network (WPAN), a wireless sensor network, a wireless local area network (WLAN), a wide area network (WAN), and/or any other suitable communications network.

In one embodiment, the sensor 202 and the monitor 204 may be configured to communicate over a designated communications link having a predefined bandwidth using a sensor transceiver 208 and a monitor transceiver 210, respectively. In one embodiment, the predefined bandwidth corresponds to a frequency spectrum specified by a statutory authority for communications between wireless medical devices, such as the sensor 202 and the monitor 204, within the communications network 206. For example, the sensor 202 may be configured to communicate with the monitor 204 over a communications link within the 2360-2400 MegaHertz (MHz) band when it is located within the designated monitoring area. However, when located outside the designated monitoring area, the sensor 202 may be configured to communicate over a communications link outside the 2360-2390 MHz band.

In certain embodiments, the sensor 202 is configured to communicate with the monitor 204 using a determined communications protocol. In one embodiment, the determined communications protocol may be stored in a sensor memory 212 and/or a monitor memory 214. To that end, the sensor memory 212 and/or the monitor memory 214 may include storage devices such as a random access memory, a read only memory, and/or solid-state storage device. Alternatively, the communications protocol may be input by a user during system setup. In certain embodiments, the determined communications protocol defines one or more instructions for establishing association with the monitor 204, transmitting patient information, contention resolution, disconnecting from the monitor 204 using a predefined termination sequence, and/or initiating loss prevention indicators.

Particularly, in one embodiment, the communications protocol defines one or more instructions to initiate a communication link for establishing an association between the sensor 202 and the appropriate monitor 204. For example, the disconnected sensor 202 and the monitor 206 may be associated using near filed communications (NFC), wireless discovery messages, and/or authentication using public or private key encryption. Additionally, the disconnected sensor 202 and the monitor 206 may be associated using touch or synchronized timer-based identification, default connection parameters, and/or any other suitable association techniques. In certain embodiments, the sensor 202 is associated with a single monitor 204 to ensure privacy and integrity of patient data. However, the monitor 204 may be associated with more than one patient monitoring sensor 202 to allow monitoring of a plurality of physiological and/or environmental indicators that may be used in clinical diagnosis and treatment.

Subsequent to association, the sensor 202 begins transmitting the patient information to the monitor 204 over a communications link, for example, designated by the monitor 204 during association. Particularly, the sensor 202 measures and transmits the patient information to the monitor 204 continuously, randomly, or at one or more determined intervals of time. To that end, the sensor 202 includes a sensor timer 216 that allows for timely measurement and/or transmission of patient information to the associated monitor 204. In one embodiment, the sensor timer 216 may be configured to determine a first time period taken to receive a communication from the monitor 206 and/or a second time period elapsed since transmitting patient information to the monitor. The first and second time period may be used to determine an association status of the sensor 202 with respect to the monitor 206. In one embodiment, for example, when both the first and second time periods are determined to be less than one or more predetermined communication thresholds, the sensor 202 and the monitor 206 are determined to be associated with each other.

When associated with the sensors 202, the monitor 206 is configured to receive the patient information and communicate the received information to a caregiver using one or more output devices 218. The output devices 218, for example, may include a display 220, an audio output device, and/or a lighting device. In certain embodiments, the monitor 204 allows the caregiver to selectively configure the patient information to be monitored and/or a frequency and form of communication of the patient information provided to the caregiver. To that end, in one embodiment, the monitor 204 includes a user interface (UI) 222 that provides the caregiver with selectable and/or input options to select the parameters of interest for monitoring. Further, the user may use the UI 222 to specify the form and frequency for communicating the received patient information to the caregiver.

Particularly, in one example, the caregiver may request a customized form of the patient information that provides more insightful information regarding a pathological condition of the patient. To that end, in one embodiment, the monitor 204 includes a monitor processing unit (MPU) 224 that analyzes the received patient information to determine medically relevant parameters and/or to communicate the determined parameters to the caregiver in a more suitable form. For example, in one embodiment, the monitor 204 displays the determined parameters on the display 220 as a textual and/or a graphical output. In certain embodiments, the user may also use the UI 222 associated with the monitor 204 to trigger a loss prevention procedure to reveal one or more of the sensors 202 that are associated with the monitor 204 but are assumed to be lost.

At times, housekeeping, patient movement, theft, and/or careless handling of the sensor 202 may result in unintentional movement of the sensor 202, thereby resulting in loss of communication between the sensor 202, the patient, and the monitor 204. Additionally, the sensor 202 in an initial state, for example out of a box or when charging, may be unassociated with the monitor 204. The sensor 202, in such a scenario, may determine itself to be lost if the sensor 202 fails to receive communication from the monitor 206 for more than a determined period of time. The loss of the sensor 202 halts patient monitoring, thereby impeding access to desired patient information typically received at the monitor 204 at determined points of time. The present disclosure allows for detection and recovery of the lost sensor 202 using existing network infrastructure available in the hospital.

In one embodiment, the caregiver detects the loss of the sensor 202 and initiates a reveal signal from the monitor 204 to the lost sensor 202, for example, by pressing an appropriate button or selecting one or more appropriate options on the UI 222. Alternatively, the monitor 204 may automatically detect loss of the sensor 202 based on time elapsed since last communication with the sensor 202. The monitor 204 may determine the time elapsed since the last communication with the sensor 202 using a monitor timer 226. Upon determining that the time since last communication with the sensor 202 is greater than a determined communications threshold, the monitor 204 assumes the sensor 202 to be lost.

Subsequently, the monitor 204 transmits a reveal signal to the sensor 202 over a predefined or the determined communications link. In one embodiment, the reveal signal includes identification parameters to ensure that only the lost sensor 202 responds to the reveal signal. In certain embodiments, the identification parameters are exchanged while establishing association between the sensor 202 and the monitor 204 to facilitate loss prevention procedures. Upon receiving the reveal signal, a sensor processing unit (SPU) 228 in the lost sensor 202 examines the identification parameters to determine if the reveal signal is received from the associated monitor 204. If the reveal signal is received from the authorized monitor 204, the SPU 228 initiates the loss prevention indictors using one or more sensor output devices 230. As previously noted, the SPU 228 may also initiate the loss prevention indictors using the output devices 230 when a link establishment procedure between the sensor 202 and another monitor is initiated without completing the predefined termination sequence with the authorized monitor 204.

In one embodiment, the output devices 230 may include devices such as a speaker, a light emitting diode (LED), and/or a motor. For example, the SPU 228 configures the output devices 230 to generate an audible alarm, blink LED lights, and/or initiate vibration, thus aiding a caregiver in the vicinity to locate and retrieve the lost sensor 202 easily. Additionally, initiating the loss prevention indicators may also allow for adherence to appropriate link management protocols by alerting a caregiver that a predefined connection establishment and/or termination sequence are not being followed with respect to the use of the sensor 202.

However, in certain scenarios, the monitor 204 may fail to receive any response to the reveal signal if the sensor 202 moves outside a communications range of the monitor 204. In one embodiment, if the monitor 204 fails to receive a response from the sensor 202 within a determined tracking threshold or after a determined number of communication attempts, the monitor 204 communicates the loss of the sensor 202 to an interrogator 232. In one embodiment, the interrogator 232 is communicatively coupled to the monitor 204 and other interrogators over the communications network 206. The interrogator 232 receives the communication from the monitor 204 via an interrogator transceiver 234. Additionally, the interrogator 232 may receive and store authentication and/or association information from the monitor 204 in an interrogator memory 236 for use in establishing a wireless connection with the lost sensor 202. Certain further embodiments may also allow use of autonomous interrogators that may be configured to listen to announce signals from lost sensors over a default communication channel even when no request from the monitor 204 is received.

In one embodiment, the interrogator 232 uses the received association information or the default communications channel to transmit a reveal signal to the lost sensor 202. To that end, the interrogator 232 includes an interrogator processing unit (IPU) 238 configured to generate the reveal signal that causes the lost sensor 202 to initiate loss prevention indicators. However, if the interrogator 232 also fails to receive a response from the sensor 202, the interrogator 232 communicates the loss of the sensor 202 to other interrogators on the communications network 206, thereby enabling a distributed search for the lost sensor 202.

In certain scenarios, the sensor 202 may not receive the reveal signals transmitted by any of the interrogators due to loss of connectivity to the communications network 206. Even in such scenarios, the sensor 202 may independently determine that the sensor 202 has lost communication with the monitor 204 and is lost. As previously noted, the SPU 228 may determine a time since last communication with the monitor 204 using the sensor timer 216. If the SPU 228 determines the time since last communication with the monitor 204 to be greater than a determined threshold, the SPU 228 may immediately initiate the loss prevention indicators to allow a caregiver to identify a location of the lost sensor 202. Subsequently, to prevent any inadvertent initiation of loss prevention indicators, the sensor timer 216 may be reset following communication of the loss prevention indicators from the sensor 202. Additionally, the sensor 216 may be reset when the sensor 202 is decoupled from the patient and/or when the sensor 202 is being charged, thus allowing for an efficient loss prevention operation.

Embodiments of the system 200, thus, allow for efficient patient monitoring by allowing for quick detection and recovery of lost patient sensors. Particularly, embodiments of the system 200 allow for cost-effective and uncomplicated loss prevention by periodically verifying association status of the patient sensor and implementing appropriate loss prevention protocols based on the determined association status.

Figure 3:
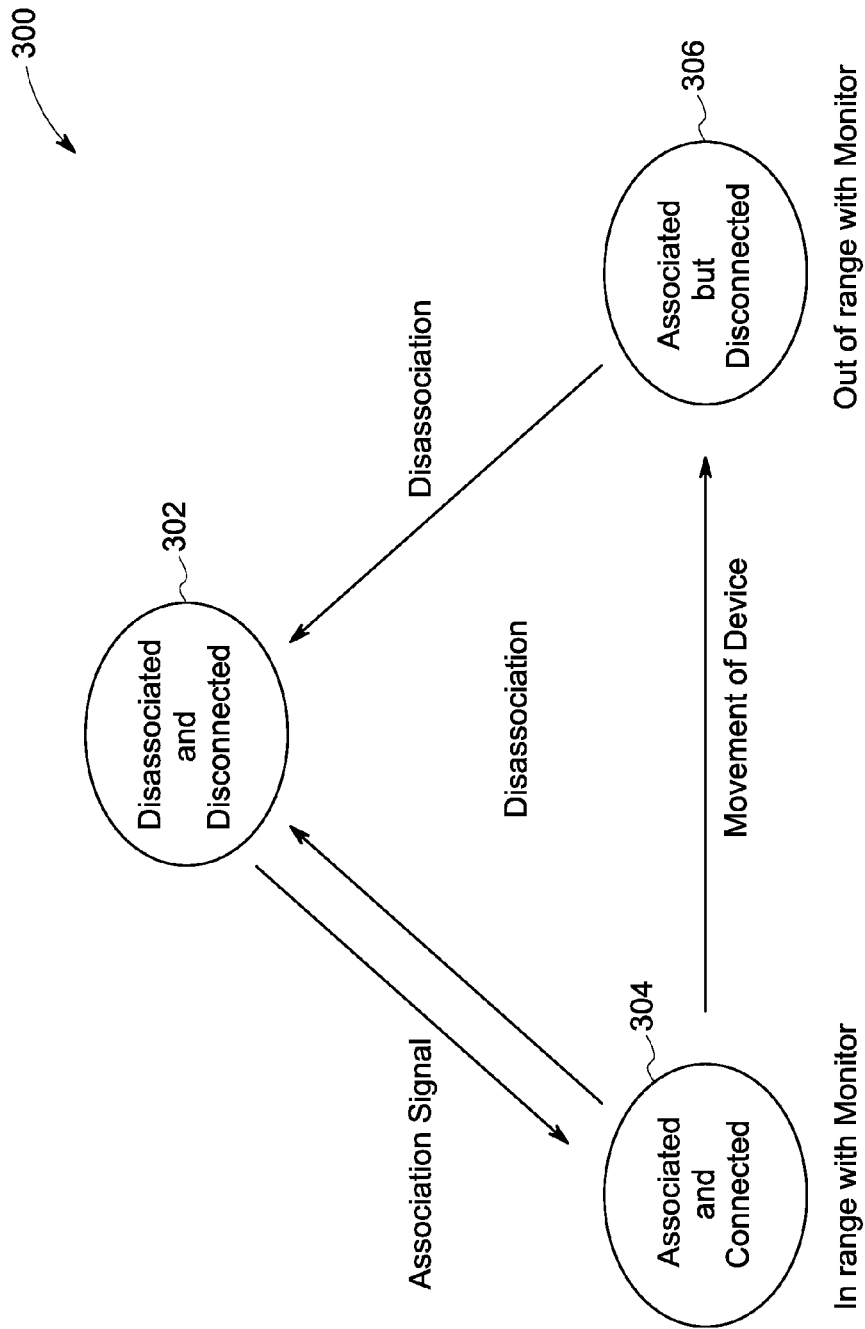
FIG. 3 is a schematic diagram illustrating exemplary association statuses of a patient sensor and a patient monitor configured to implement loss prevention procedures, in accordance with aspects of the present disclosure.

FIG. 3 illustrates a schematic diagram 300 illustrating exemplary association statuses of a patient sensor and a patient monitor configured to implement loss prevention procedures, in accordance with aspects of the present disclosure. In FIG. 3, element 302 corresponds to a disassociated and disconnected status of a patient sensor such as the sensor 102 of FIG. 1 and/or the sensor 202 of FIG. 2. The association status 302 corresponds to an initial state of the patient sensor when the patient sensor is either charging or is listening for an association signal. In certain embodiments, such a disassociated and disconnected patient sensor may periodically reveal itself by activating loss prevention indicators. Specifically, the patient sensor may transmit an "announce" signal using its wireless transmitter on a predetermined and/or a default frequency channel at a periodic interval.

Moreover, on receiving the association signal, the patient sensor exchanges association messages with the patient monitor and establishes an association and/or pairing. Further, the patient sensor begins transmission of patient information to the patient monitor, thus progressing to an associated and connected status, as depicted by element 304. However, in certain scenarios, the patient sensor may be assumed to be lost even when the patient sensor is associated and connected to the patient monitor. For example, when the patient sensor is able to communicate over the wireless network but is not visible to a caregiver, the caregiver may trigger the patient sensor to initiate loss prevention indicators by configuring appropriate options on a UI of the patient monitor. Upon receiving the user instructions, the patient monitor may be configured to broadcast a "reveal" signal to all sensors that are connected and associated to the wireless network. Alternatively, the patient monitor may be configured to transmit the reveal signal to a specific patient sensor determined to be lost.

Furthermore, when a patient sensor associated with the patient monitor gets lost due to unintentional movement outside a communications range of the patient monitor, the patient sensor moves to an associated but disconnected status, as indicated by element 306. The patient sensor may still use its wireless receiver capability to listen for the reveal signal from or an interrogator or the patient monitor. Upon receipt of the reveal signal addressed to itself or all sensors on the wireless network, the patient sensor transmits the announce signal and reveals itself by activating one or more loss prevention indicators. In one embodiment, the patient sensor may be configured to listen for reveal signal more often than autonomously transmitting the announce signal. The announce signal may be wirelessly received by an interrogator or the patient monitor. Particularly, in certain embodiments, frequency diversity may be implemented by the system 200 such that interrogators transmit the reveal signal using a first frequency, whereas the patient sensor transmits the announce signal using a second frequency. Furthermore, in a distributed searching scenario, if multiple devices receive the announce signal from a patient sensor then the location of the lost patient sensor may be determined by analyzing signal strength of the received announce signal. Embodiments of the system 200, thus, allow for extension of an existing network infrastructure for use in efficiently locating lost sensors, even when the lost sensors may not be in communication with other hospital devices. An exemplary method for loss prevention of wireless devices from a designated area is described in greater detail with reference to FIG. 4.

Figure 4:
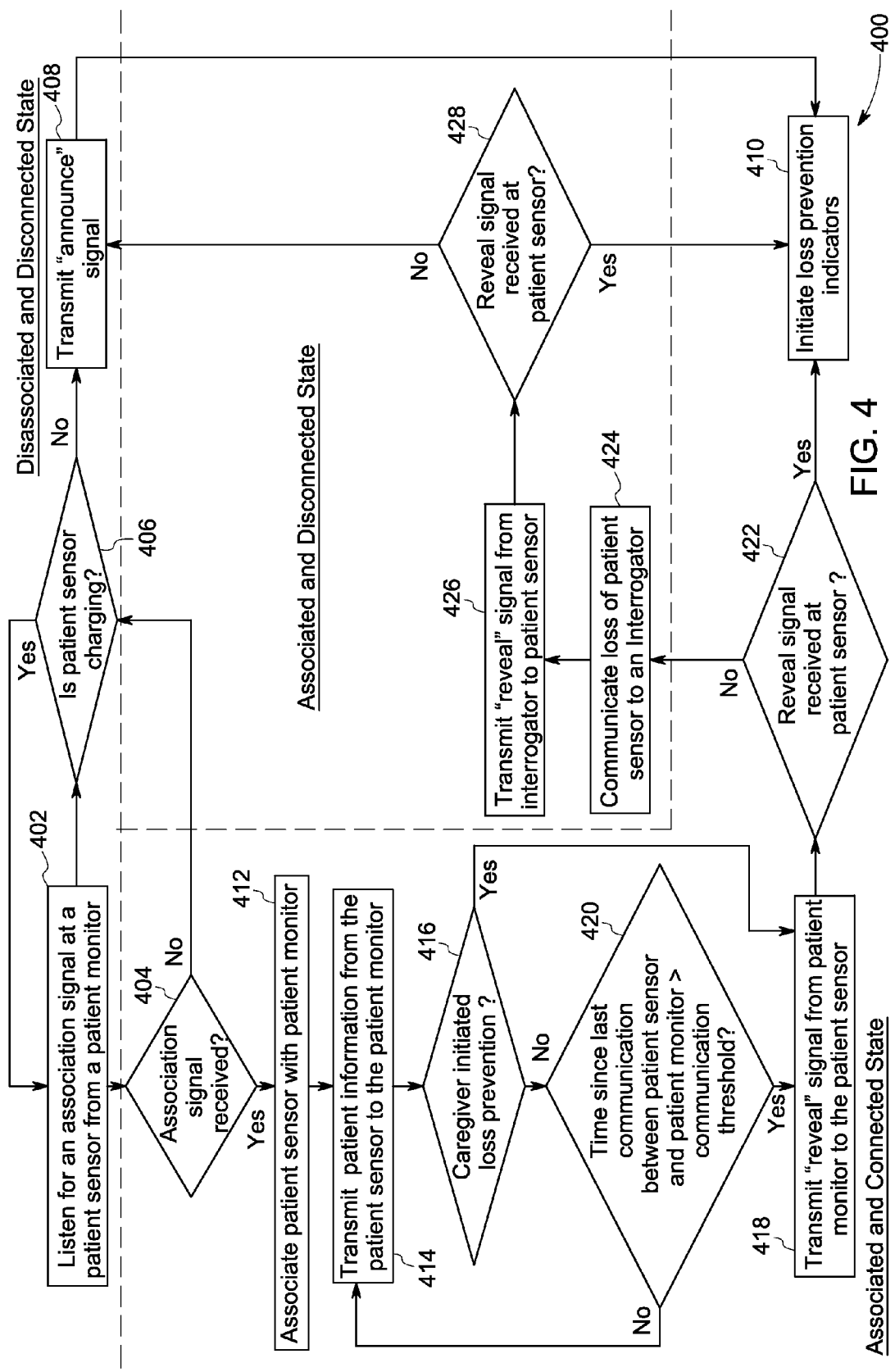
FIG. 4 is a flow chart illustrating an exemplary method for managing patient monitoring devices, in accordance with aspects of the present disclosure.

FIG. 4 illustrates a flow chart 400 depicting an exemplary method for managing patient monitoring devices. In the present disclosure, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract data types.

Additionally, embodiments of the exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 4, the exemplary method is illustrated as a collection of blocks in a logical flow chart, which represents operations that may be implemented in hardware, software, or combinations thereof. The various operations are depicted in the blocks to illustrate the functions that are performed, for example, during the steps corresponding to detecting loss of the patient sensor, initiating one or more loss prevention indicators, and communicating the loss prevention indicators in the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-2.

Embodiments of the present disclosure allow for management of patient sensors in a designated monitoring area. Particularly, embodiments described herein allow for detection of a lost patient sensor without use of additional tracking devices and/or network infrastructure. For clarity, the embodiment of the method depicted in FIG. 4 describes exemplary implementations of the loss prevention procedures at different association statuses of the patient sensor and a patient monitor.

Initially, the patient sensor may be in an initial state, where the patient sensor is disassociated and disconnected from the patient monitor. Accordingly, at step 402, the patient sensor listens for an association signal from the patient monitor. In one embodiment, the patient sensor may periodically monitor a default communication channel to listen for the association channel. The default communication channel may be defined, for example, during system setup.

At step 404, it may be determined if the association signal is received. If no association signal is received, at step 406, it may be determined if the patient sensor is in a charging state. If it is determined that the patient sensor is charging, in one embodiment, the patient sensor is assumed to be still in the initial state. However, if the patient sensor is not charging, the patient sensor may assume itself to be lost. Accordingly, at step 408, the patient sensor transmits the announce signal over a designated communications link. Additionally, at step 410, the patient sensor initiates one or more loss prevention indicators. The loss prevention indicators may include an audible alarm, blinking lights, and/or transmission of an alert message to a designated phone number.

However, if the association signals are received at step 404, the patient sensor is associated with the patient monitor using the received association signals, as depicted by step 412. In one embodiment, the patient sensor is associated with the patient monitor, for example, using NFC, wireless discovery messages, and/or default authentication details. Subsequently, the patient sensor moves into an associated and connected state.

Subsequent to the association, at step 414, the patient sensor begins transmitting the patient information to the patient monitor. In one embodiment, the patient sensor communicates the patient information to the patient monitor continuously. In another embodiment, the patient sensor communicates the patient information to the patient monitor at designated intervals. Alternatively, the patient sensor communicates the patient information to the patient monitor non-periodically. For example, the patient sensor communicates the patient information to the patient monitor upon detecting that a physiological parameter such as pulse or respiration rate corresponding to the patient is outside a designated range.

As previously noted, the small and lightweight patient sensor may get lost within or outside the patient monitoring region, thereby losing communications with the patient monitor. For example, the patient sensor may fall to the floor, in a bathroom, or behind a bed, and thus, may not be visible to a caregiver. Alternatively, the patient sensor may get lost in dirty laundry and may be unintentionally routed to a laundry cleaning facility, thus ceasing to transmit patient information to the patient monitor. Furthermore, careless handling of the patient sensor may result in unintentional movement of the patient sensor out of the designated monitoring area such as the hospital.

In certain scenarios, the caregiver may detect a loss of the patient sensor or assume the patient sensor to be lost if the patient sensor is not visible to the caregiver. In such scenarios, the caregiver may trigger the loss prevention indicators in the patient sensor by configuring appropriate options on a UI of the patient monitor. Accordingly, at step 416, it may be determined if the caregiver has initiated loss prevention indicators. If it is determined that the caregiver has initiated loss prevention indicators, the patient monitor transmits a "reveal" signal to the patient sensor, as depicted by step 418. However, if no such caregiver input is received at step 416, control passes to step 420.

At step 420, it may be determined if a time since last communication between patient sensor and patient monitor is greater than a determined communication threshold. In one embodiment, determined communication threshold, for example, may be about 15 minutes. The communications threshold, however, may be defined differently for different patient sensors. Moreover, the communications threshold may be defined, for example, during setup or during association of the patient sensor to the patient monitor.

If the time since last communication is less than the determined communications threshold, the patient sensor may continue transmitting patient information to the patient monitor, as depicted by step 414. However, if the time since last communication is greater than the determined communications threshold, the patient monitor transmits a "reveal" signal to the patient sensor, as depicted by step 418. Additionally, the patient monitor may transmit the reveal signal to a specific node or to all nodes using unicast or broadcast addressing, respectively. Control may then pass to step 422.

At step 422, it may be determined if the reveal signal is received at the patient sensor. When the patient sensor is within a communications zone of the patient monitor, the patient sensor may receive the reveal signal and initiate loss prevention indicators, as depicted by step 410. However, if the patient sensor has moved out of the communications zone of the patient monitor, the patient sensor may fail to receive the reveal command. The patient monitor may determine that the reveal signal is not received by the patient sensor if the patient monitor fails to receive any response from the patient sensor over the wireless link within a tracking threshold, for example, of about two minutes or after a determined number of communications attempts.

The patient monitor may then communicate the loss of patient sensor to an interrogator, as depicted by step 424. Additionally, in certain embodiments, the monitor 106 provides the interrogator with association information such as frequency range and/or authentication parameters that would allow the interrogator to establish communications with the lost patient sensor. Alternatively, the interrogator may use default association parameters that may be available to all devices connected over the wired and/or wireless communications network. To that end, the interrogator may be communicatively coupled to the patient monitor over an existing wired and/or wireless network in the designated monitoring area. Further, one or more interrogators may be disposed at different regions in the designated monitoring area, for example, at gates and exits to prevent movement of the patient sensor outside the designated monitoring area.

Particularly, in one embodiment, the interrogator may transmit, for example, a beacon message to announce its identity to proximate patient monitors and/or patient sensors. Specifically, the interrogator may transmit the beacon signal on a default channel accessible to the patient sensors and/or the patient monitors. The patient sensors, in turn, may be configured to synchronize their announce signals or responses to reveal signals based on the beacon signal. In certain embodiments, the beacon signal may include information for use by the patient sensors to transmit reveal messages in either determined time slots or shared time slots. Further, the beacon signal may also include contention-based protocols for use by the patient sensors and/or the patient monitors, for example, for contention resolution during communication.

Further, at step 426, the interrogator may transmit a reveal signal to the patient sensor. Particularly, in one embodiment, the interrogator uses the beacon signal and/or the default association information to transmit the reveal signal to the lost patient sensor over a suitable communications channel. At step 428, it may be determined if the reveal signal is received at the patient sensor. When the patient sensor is within a communications zone of the interrogator, the patient sensor may receive the reveal signal and initiate loss prevention indicators, as depicted by step 410 to allow a caregiver to locate the lost sensor easily.

In certain embodiments, the interrogator may also convey information to the patient sensor indicating a current location of the patient sensor. For example, an interrogator placed near an exit door may cause the patient sensor to reveal itself, while also informing the patient sensor that it is located at an exit. Such location knowledge may cause the patient sensor to modify its wireless transmit & receive configurations to adhere to statutory provisions. Alternatively, the patient sensor may adjust periodic rates at which the patient sensor autonomously reveals itself or listens for "reveal" command messages. In one embodiment, different periodic rates for the patient sensor may be triggered based on a distance of the patient sensor from the exit.

However, if the patient sensor has moved out of the communications zone of the interrogator, the patient sensor may fail to receive the reveal command, thus moving to a disconnected state. In accordance with aspects of the present disclosure, upon determining a prolonged absence of communications with the patient monitor, the patient sensor transmits the announce signal and periodically reveals itself by activating loss prevention indicators, as depicted by step 408.

Although an interrogator communicatively coupled to the patient monitor is described herein, in certain embodiments, an autonomous interrogator configured to actively listen for "announce" signals from a lost patient sensor may also be employed. Particularly, in one embodiment, the autonomous interrogator may be configured to listen for the announce signals from the patient sensor irrespective of whether the patient sensor is associated with a patient monitor, or is disassociated and lost. The announce signal may be wirelessly received by an interrogator or the patient monitor. Furthermore, in a distributed searching scenario, if multiple interrogators receive the announce signal from a patient sensor then the location of the patient sensor may be determined by analyzing signal strength of the received announce signal. In one embodiment, the announce signal includes the patient sensor's network address or hardware device identification number to allow for easy detection of the lost patient sensor.

In one embodiment, the interrogator may be configured to trigger one or more loss prevention indicators in the lost patient sensor upon receiving the announce message from the lost sensor. Alternatively, the interrogator may be configured to output the loss prevention indicators itself, so as to indicate that a lost patient sensor is present in its vicinity. Such an autonomous interrogator may be powered by a proximal power source and may be capable of providing more efficient lost prevention indicators than the lost sensor without use of any additional infrastructure.

Embodiments of the present disclosure, thus, allow for efficient loss prevention techniques that employ existing wired and/or wireless communications infrastructure in a designated monitoring area to prevent loss of patient monitoring sensors. Particularly, the embodiments described herein present cost-effective systems and methods that reduce electronic board space and programming complexity by utilizing the existing communications network for both loss prevention and transmission of patient information. Use of the same wireless network allows for a cost-effective implementation of the present systems without incurring any extra cost associated with use of a separate location and/or communications infrastructure.

Additionally, the present disclosure allows for both autonomous and triggered reveal and announce capabilities to actuate audible and/or visual indicators that aid in swift detection and retrieval of lost patient sensors. Retrieval and restoration of the patient sensors allows for continuous and real-time access to comprehensive patient information at a point of care. Specifically, the real-time access to the patient information facilitates early detection of deterioration of health of a patient, thus allowing for timely intervention and/or making informed clinical decisions.

It may be noted that the foregoing examples, demonstrations, and process steps that may be performed by certain components of the present systems, for example by the SPU 228, the MPU 224, and/or the IPU 238 of FIG. 2, may be implemented by suitable code on a processor-based system. To that end, the processor-based system, for example, may include a general-purpose or a special-purpose computer. It may also be noted that different implementations of the present disclosure may perform some or all of the steps described herein in different orders or substantially concurrently.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of embodiments of the present disclosure may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and methods for use in patient monitoring.

While only certain features of the present disclosure have been illustrated and described herein, many modifications and changes will occur to those skilled in the art. It is, therefore, to be understood that the appended claims are intended to cover all such modifications and changes as fall within the true spirit of the invention.

The invention claimed is:

1. A body worn patient sensor, comprising:
    a sensor transceiver configured to transmit patient information to a patient monitor over a communications network available in a designated monitoring area;
    a sensor processing unit configured to initiate one or more loss prevention indicators upon receiving a reveal signal from the patient monitor, upon failing to receive communication from the patient monitor for more than a determined period of time, or a combination thereof;
    one or more sensor output devices configured to communicate the loss prevention indicators to indicate location of the patient sensor that is lost; and
    at least one interrogator coupled to the communications network is configured to:
    listen for an announce signal from the patient sensor, a request from the patient monitor, or a combination thereof, over a default communications channel in the communications network; and
    communicate one or more loss prevention indicators to indicate location of the patient sensor upon receiving the announce signal from the patient sensor.

2. The body worn patient sensor of claim 1, wherein the sensor processing unit is further configured to initiate the loss prevention indicators upon receiving a reveal signal from an interrogator over a designated communications channel in the communications network.

3. The body worn patient sensor of claim 2, wherein the interrogator is communicatively coupled to the patient monitor, the body worn patient sensor, or a combination thereof, over the communications network.

4. The body worn patient sensor of claim 2, wherein the interrogator is an autonomous device.

5. The body worn patient sensor of claim 2, wherein the sensor processing unit is configured to initiate the loss prevention indicators upon receiving an association request from another patient monitor.

6. The body worn patient sensor of claim 2, wherein the sensor transceiver is configured to the transmit the announce signal indicative of a loss of the body worn patient sensor to the patient monitor, the interrogator, or a combination thereof, over the designated communications channel.

7. The body worn patient sensor of claim 1, further comprising a timer configured to determine a first time period taken to receive a communication from the patient monitor, a second time period elapsed since transmitting patient information to the patient monitor, or a combination thereof.

8. The body worn patient sensor of claim 7, wherein the sensor processing unit is configured to reset the timer when the body worn patient sensor is decoupled from a patient, when the body worn patient sensor is being charged, following communication of the loss prevention indicators, or combinations thereof.

9. The body worn patient sensor of claim 1, wherein the communications network corresponds to a pre-existing communications network available in the designated monitoring area.

10. The body worn patient sensor of claim 1, wherein the patient monitor is configured to transmit the reveal signal to the patient sensor to initiate one or more loss prevention indicators upon receiving user instructions, upon failing to receive communication from the patient sensor for more than a determined period of time, or a combination thereof.

11. The body worn patient sensor of claim 1, wherein the patient monitor is further configured to request at least one interrogator to transmit a reveal signal to the patient sensor upon failing to receive a response to the reveal signal from the patient sensor within a determined tracking threshold, wherein the interrogator is communicatively coupled to the patient monitor over the communication network.

12. The body worn patient sensor of claim 1, wherein the communications network comprises a sensor network, wherein the sensor network further comprises a wireless network, a wired network, or a combination thereof.

13. A method for managing patient monitoring devices, comprising:
    transmitting patient information from a patient sensor operatively coupled to a patient to a patient monitor, wherein the patient sensor and the patient monitor are communicatively coupled over a communications network available in a designated monitoring area;
    detecting loss of the patient sensor from the designated monitoring area by one or more of the patient sensor, the patient monitor and a user;
    initiating one or more loss prevention indicators at the patient sensor upon detecting the loss of the patient sensor;
    communicating the loss prevention indicators to indicate location of the patient sensor that is lost;
    requesting one or more of the interrogators to transmit a reveal signal to the patient sensor; and
    receiving location information corresponding to the patient sensor from at least one of the interrogators that receives an announce signal from the patient sensor in response to the reveal signal.

14. The method of claim 13, further comprising communicatively coupling the patient sensor to the patient monitor using near field communication, exchange of wireless discovery messages, encryption keys, or combinations thereof.

15. The method of claim 14, wherein communicatively coupling the patient sensor to the patient monitor comprises exchanging one or more communications parameters for transmitting and receiving patient information, transmitting the one or more reveal signals, initiating the loss prevention indicators, associating the patient sensor to the patient monitor, terminating an association between the patient monitor and the patient sensor, or combinations thereof.

16. The method of claim 15, wherein initiating the one or more loss prevention indicators comprises transmitting the reveal signals from the patient monitor to the patient sensor for initiating the loss prevention indicators if the period of time since the last communication between the patient monitor and the patient sensor is greater than a determined communication threshold.

17. The method of claim 16, wherein transmitting one or more reveal signals comprises communicating loss of the patient sensor to one or more interrogators communicatively coupled to the patient monitor over the communications network when no loss prevention indicators are detected by the patient monitor within a determined tracking threshold in response to the reveal signals.

18. The method of claim 17, wherein the communications network corresponds to a medical body area network, and wherein the patient sensor is configured to communicate using a designated communications link having a bandwidth corresponding to a frequency spectrum specified by a statutory authority for communications within the medical body area network.

19. The method of claim 18, further comprising reconfiguring the patient sensor to communicate over a communication link having a bandwidth outside the frequency spectrum upon detecting that the patient sensor is outside the designated monitoring area.

20. The method of claim 13, wherein detecting the loss of the patient sensor comprises receiving one or more user instructions indicative of the loss of the patient sensor via a user interface associated with the patient monitor.

21. The method of claim 13, wherein detecting loss of the patient sensor comprises determining whether a period of time since the last communication between the patient monitor and the patient sensor is greater than a determined communication threshold.

22. A non-transitory computer readable medium that stores instructions executable by one or more processors to perform a method for managing patient monitoring devices, comprising:
    transmitting patient information from a patient sensor operatively coupled to a patient to a patient monitor, wherein the patient sensor and the patient monitor are communicatively coupled over a communications network available in a designated monitoring area;
    detecting loss of the patient sensor from the designated monitoring area by one or more of the patient sensor, the patient monitor and a user;
    initiating one or more loss prevention indicators at the patient sensor upon detecting the loss of the patient sensor;
    communicating the loss prevention indicators to indicate location of the lost patient sensor and
    at least one interrogator coupled to the communications network is configured to:

listen for an announce signal from the patient sensor, a request from the patient monitor, or a combination thereof, over a default communications channel in the communications network; and communicate one or more loss prevention indicators to indicate location of the patient sensor upon receiving the announce signal from the patient sensor.

* * * * *